United States Patent [19]

Rebuffat et al.

[11] Patent Number: 4,915,107
[45] Date of Patent: Apr. 10, 1990

[54] AUTOMATIC INSTRUMENT FOR PURSE-STRING SUTURES FOR SURGICAL USE

[75] Inventors: Carlo Rebuffat; Riccardo Rosati, both of Milan, Italy

[73] Assignee: Harley International Medical Ltd., London, United Kingdom

[21] Appl. No.: 316,299

[22] Filed: Feb. 27, 1989

[30] Foreign Application Priority Data

Mar. 9, 1988 [IT] Italy ................. 19712 A/88

[51] Int. Cl.$^4$ ............................................. A61B 17/06
[52] U.S. Cl. .................................................. 606/144
[58] Field of Search ........................... 128/340, 334 R

[56] References Cited

U.S. PATENT DOCUMENTS

| | | | |
|---|---|---|---|
| 3,842,840 | 10/1974 | Schweizer | 128/340 |
| 4,164,225 | 8/1979 | Johnson et al. | 128/334 R |
| 4,236,470 | 12/1980 | Stenson | 112/169 |
| 4,471,781 | 9/1984 | Di Giovanni | 128/334 R |
| 4,553,544 | 11/1985 | Nomoto et al. | 128/340 |
| 4,621,640 | 11/1986 | Mulhollan et al. | 128/340 |

FOREIGN PATENT DOCUMENTS

| | | | |
|---|---|---|---|
| 0119967 | 9/1984 | European Pat. Off. | 128/334 R |
| 156440 | 6/1939 | Fed. Rep. of Germany | 128/340 |
| 2081099 | 2/1982 | United Kingdom | 128/334 R |

*Primary Examiner*—Edward M. Coven
*Assistant Examiner*—Gary Jackson

[57] ABSTRACT

This invention relates to an automatic instrument for purse-string sutures for surgical use, comprising two toothed jaws provided with openings having side slots for through passage of the needles carrying the ends of a suture thread fastened thereto. Said jaws are integral with a pair of support members adapted to be opened in order to be able to introduce the part to be sutured therebetween. Said support members carry a pair of flexible wires having one end wound around a pair of coaxial drums controlled by means of a knob, while the opposite ends are each connected to a needle, in such a way that by actuating the knob, the flexible wires unwind from the drums and push the needles through the jaw openings all the way to make the needle ends to project out of the ends of the jaws.

12 Claims, 3 Drawing Sheets

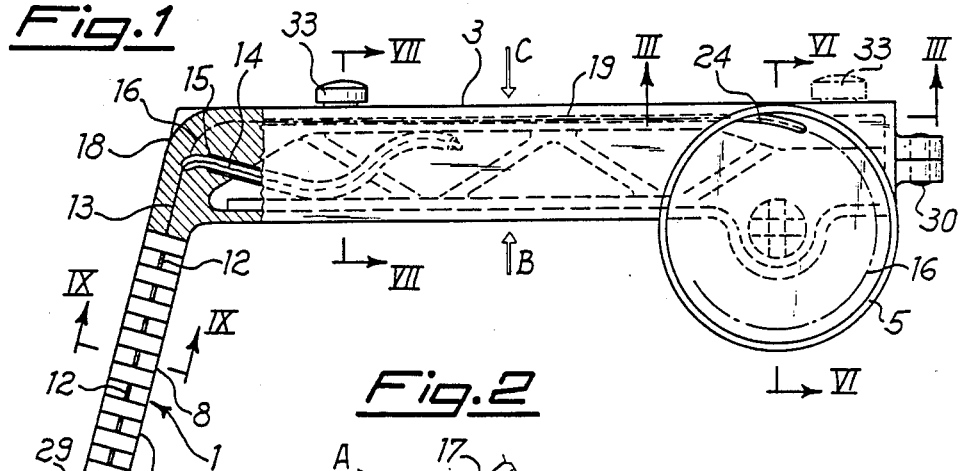
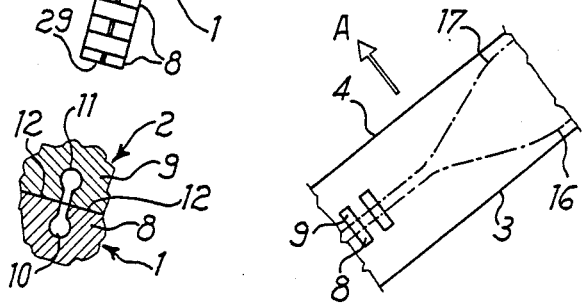
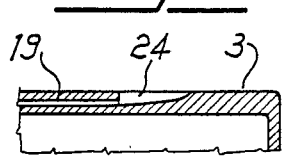
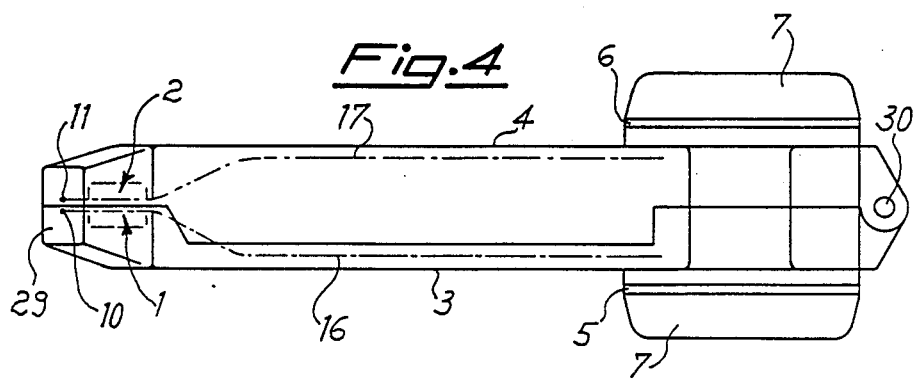
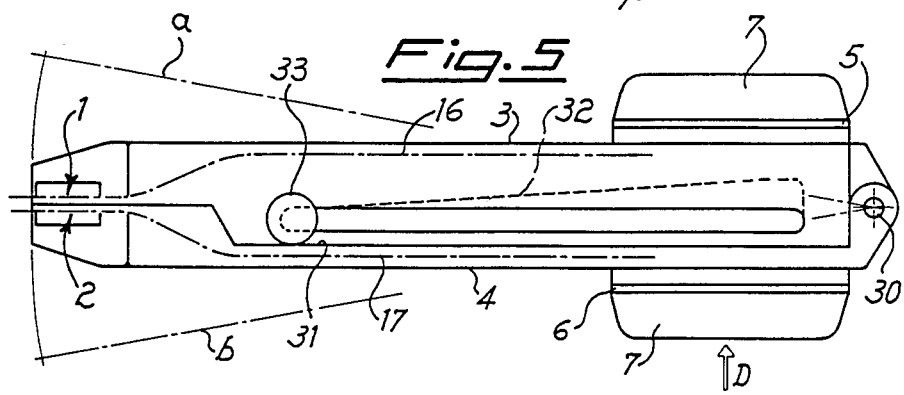

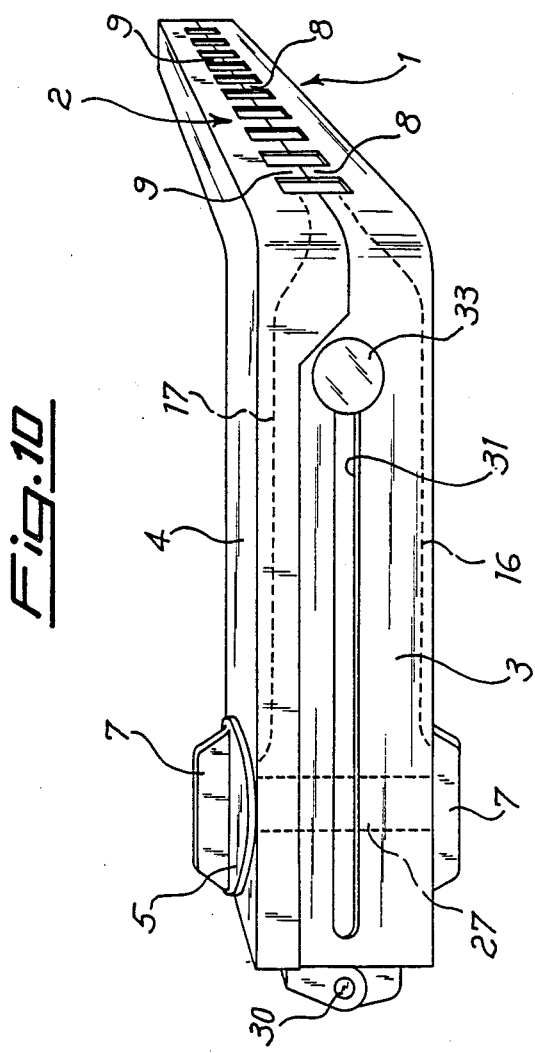

AUTOMATIC INSTRUMENT FOR PURSE-STRING SUTURES FOR SURGICAL USE

This invention relates mainly to an automatic instrument for the so called "purse-string" sutures, for surgical use, including two toothed jaws, the instrument being usable in narrow spaces and in deep spots, without requiring the needles to be manually inserted into said jaws.

As it is known, in order to be able to take advantage of the circular mechanical suturing instruments which have been known for some time in the surgical field, it has been necessary to resort to the so called "purse-string" type sutures.

A suture of the subject type does not involve particular difficulty and can be performed quite quickly, when operating in areas which are neither narrow nor positioned at a depth. In the above conditions said sutures may be made manually or mechanically, using the straight toothed jaw instruments, provided with openings through which one or more needles are manually slid, along one of the jaws in a first direction and subsequently along the second jaw in the opposite direction. Said instrument, which is described in British Patent No. 2 081 099, has a drawback, in that it can be used only in wide operating areas, wherein the instrument can be inserted and the straight needle can be slid through the openings provided for that purpose on the jaws.

In order to overcome said difficulties there has been studied an instrument provided with two jaws extending along an arc, and supported by arms which are arc shaped as well. Said instrument is disclosed in European Patent No. 0119 967 and, while it is improved compared to the instrument disclosed in British Patent No. 2 081 099, still doesn't completely solve all the problems related to the purse-string suture technique: in fact, in this case as well, the needles have to be inserted manually, and the operation may prove difficult in the narrower surgical spaces.

As it is apparent, to an extended needle length there corresponds a large surgical area required, therefore the technical problem to be solved was one of providing an automatic short needle instrument, in order to be able to use said instrument in narrow areas.

Therefore, a main object of this invention is to find a solution to the technical problem outlined above, in order to eliminate the drawbacks of the above mentioned instruments already known, and to provide an instrument having the following advantages:

possibility to automatically slide the needles through the openings in the jaws, i.e. without having to manually pass the needles through the openings;

possibility to use reduced length needles, said needle length in particular being no shorter than the length of the slots between adjacent jaw teeth; and possibility to use straight jaws, whose manufacturing cost is lower compared to arc-shaped jaws.

The object and the advantages mentioned above are thouroughly reached by means of the subject instrument, characterized in that support means integral with the toothed jaws are provided with two members which, at one end thereof are connected to a knob, while at the opposite end they are each connected to a surgical needle, whereby actuation of said knobs causes the needles to be pushed by said means along the openings in said jaws, to a point where the needle tips come out of the free ends of said jaws.

A further feature is the fact that said knob is integrally associated with a pair of coaxial drums and the above mentioned means, which comprise a pair of flexible wires, are winding around said drums in the disabled position of said knob, while they unwind upon operation of the knob, in order to push the flexible wires through the openings in the jaws.

Further features and advantages of this invention will become apparent from the following detailed description of a preferred although non exclusive embodiment of the subject instrument, which is also shown merely for exemplary and non limiting purposes in the attached drawing, wherein:

FIG. 1 shows a longitudinal section of the subject instrument;

FIG. 2 shows a partial view of the instrument of FIG. 1, looking in the direction of arrow A;

FIG. 3 shows a partial cross section of the instrument along line III—III of FIG. 1;

FIG. 4 is a view of the instrument shown in FIG. 1, looking in the direction of arrow B;

FIG. 5 is a view of the instrument shown in FIG. 1, looking in the direction of arrow C;

FIG. 9 is a partial cross section of both jaws along line IX—IX of FIG. 1.

Figure 6:
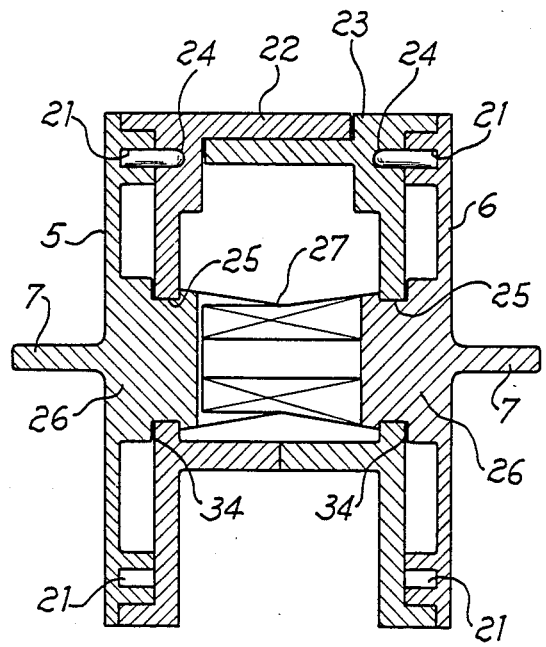
FIG. 6 is an enlarged scale cross section of the instrument, according to line VI—VI of FIG. 1.

Referring now to the attached drawing, the subject instrument comprises substantially two toothed jaws 1 and 2, integral with a pair of supporting members 3 and 4 associated with a pair of drums 5 and 6 provided with a knob 7. Jaws 1 and 2 are provided with teeth 8 and 9 respectively, wherein as it is clearly shown in FIG. 9, openings 10 and 11 are provided, in turn having side slots 12. Needles 13, only one of which is shown in FIG. 1, are inserted through said openings 10 and 11, and the ends of a suture thread 14 contained in a small protection tube 15 located between supporting members 3 and 4, are fastened to said needles.

Control members are provided under the form of flexible wires 16 and 17 which, at one end thereof, are each connected to drums 5 and 6, while at the opposite end they are fastened to needles 13.

Figure 7:
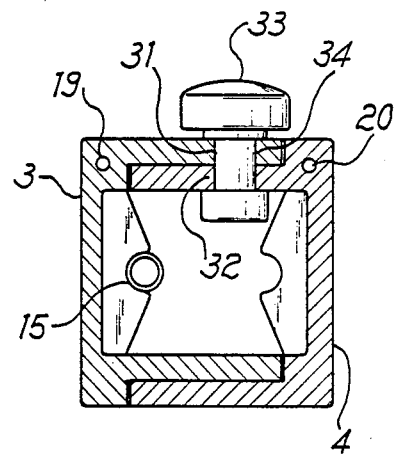
FIG. 7 is an enlarged scale cross section of the instrument, along line VII—VII of FIG. 1.
Figure 8:
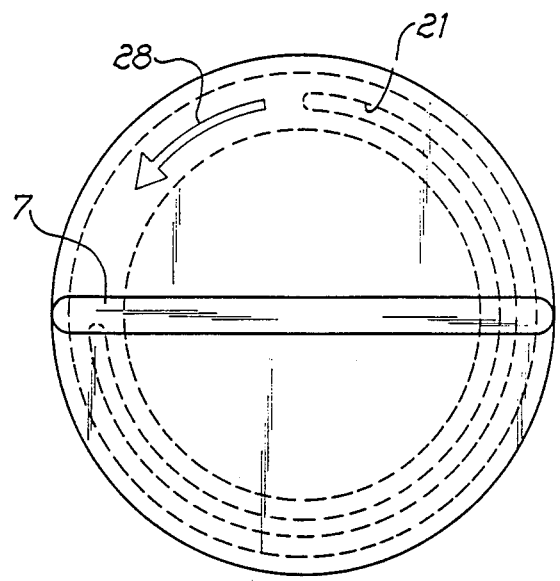
FIG. 8 is a detail of the instrument of FIG. 5, shown in the direction of arrow D.

As it should be noted, jaws 1 and 2 form an angle with the supporting members 3 and 4 thereof, and this enables the instrument to be inserted through narrow areas, and a transition portion 18, shaped as an arc of a circle is provided between the jaws and the support members, so that flexible wires 16 and 17 follow an arc shaped path at said circular transition portion, while they extend straight through two thin channels 19 and 20 towards drums 5 and 6. Said thin channels 19 and 20, wherein flexible wires 16 and 17 are slidably mounted, can be provided at the molding stage of said support members 3 and 4, or else they can be attached to the latter in the form of small tubes. As it is shown in FIGS. 1, 3 and 6, drums 5 and 6 are provided with circumferential slots 21, preferably extending along a 270° arc, wherein wires 16 and 17 are wound. Said slots 21 are closed by stationary covers 22 and 23 provided with short slots 24 connected with thin channels 19 and 20 which slidably receive flexible wires 16 and 17. Said stationary covers 22 and 23 have a central opening 25 and hubs 26, integral with drums 5 and 6, are received through said opening and are provided with suitable coupling means 27 in order to rigidly connect said drums 5 and 6 to each other. Therefore the latter will be rotated as a whole by means of either one of knobs 7, according to the direction of arrow 28, shown in FIG. 8, whereby said flexible wires 16 and 17 unwind from said circumferential slots 21 and they are slid along thin channels 19 and 20, in order to push needles 13 together with suture thread 14 along openings 10 and 11 of jaws 1 and 2, until they come out of the free ends 29 of said jaws 1 and 2. Since the jaws are straight, the needles as well are straight and very short compared to those known in the art, in that they are automatically pushed by flexible wires 16 and 17 along the whole length of jaws 1 and 2, until they project out of free ends 29 of said jaws. However, the needle length must not be shorter than the length of the cavities between pairs of jaw teeth, in order to make sure that the needles enter correctly into jaw openings 10 and 11. As it is shown in FIGS. 5 and 7, to allow jaws 1 and 2 to open, overlapping support members 3 and 4 are hingedly connected to each other at 30 and they are provided with a constant width longitudinal slot 31 and with an underlying slot 32, having the same width of slot 31 at the end thereof on the side of jaws 1 and 2, while in the direction towards the support members hinge connection, said second slot 32 is gradually widening.

In that way, a control knob 33, having a shank slidably mounted in the pair of overlapping slots 31 and 32, makes the pair of jaws to close when it is brought to the position where both slots have the same width, i.e. the position of knob 33 shown in FIG. 5.

Conversely, at the position of maximum width of the variable width slot, i.e. the position of knob 33 shown in dashed lines in FIG. 1, support members 3 and 4 and therefore also jaws 1 and 2, can be opened until the axes thereof reach positions a and b, as it is shown in FIG. 5. As it is known, opening of the jaws enables the anatomical tissues to be sutured, to be pinched therebetween, and after that the jaws are closed, in this case, just by displacing control knob 33 from the dashed line position to the solid line position in FIG. 1. Between drums 5 and 6 and respective stationary covers 22 and 23 there is provided a saw teeth retaining system just outlined in FIG. 6 and shown at 34, to prevent the drums from rotating in a direction opposite to the flexible wires 16 and 17 unwinding direction from circumferential slots 21 according to arrow 28. The diameter of said circumferential slots is such that, when knob 7 is rotated three quarters of a turn, flexible wires 16 and 17, and therefore straight needles 13 move forward approximately 80 mm, whereby the latter can project out of ends 29 of jaws 1 and 2.

For example, suture thread 14 is about 0,3 mm in diameter, slots 12 are approximately 0,4 mm high, flexible wires 16 and 17 are about 0,5 mm in diameter, and the diameter of the passage openings for needles 13 is about 1 mm. In other words, the suture thread has a diameter smaller than the height of the slots, the latter height being smaller than the flexible wire diameter, which is in turn smaller than the needle passage opening diameter, this arrangement being provided in order that suture thread 14 be able to come out of slots 12 when it is pulled by means of needles 13 passing through openings 10 and 11 of teeth 8 and 9 while being prevented to come out of slots 12.

A modified embodiment of the subject instrument, not shown in the drawings, provides for a disposable central plastic material core, provided with flexible wires 16 and 17, with needles 13 and with suture thread 14. Said central core is enclosed between the pair of support members 3 and 4 which can be made out of metal in this case, provided with jaws 1 and 2 and with control drums 5 and 6, the feature being in this case that said support members are adapted for permanent use, each time with a new central core.

Practical or embodimental modifications of construction details can be made to this invention, without exceeding the inventive concept thereof, as defined in the attached claims.

What we claim is:

1. An automatic instrument for purse-string sutures for surgical use, including two jaws (1, 2) having teeth (8, 9) provided with openings (10, 11) having a side slot (12), each of said openings (10, 11) being adapted to receive a needle (13) passing therethrough, the ends of a suture thread (14) being fastened to said needles (13), said jaws (1, 2) being integral with support members (3, 4) adapted to be opened in order to be able to introduce the part to be sutured between said jaws, characterized in that said support members (3, 4) are provided with a pair of control means which at one end thereof are fastened to a knob (7) while at the opposite end they are each fastened to a needle (13) in such a way that, by actuating said knob (7), needles (13) are pushed by said means along openings (10, 11) provided through jaws (1, 2), all the way to make needles (13) to project out of the free ends (29) of said jaws (1, 2).

2. The instrument of claim 1, characterized in that said knob (7) is integrally fastened to a pair of coaxial drums (5, 6), said control means comprising a pair of flexible wires (16, 17) being wound around said drums in the disabled position of said knob, while they unwind when said knob (7) is operated for the purpose of pushing said flexible wires (16, 17) along openings (10, 11) of jaws (1, 2).

3. The instrument of claim 2, characterized in that both jaws (1, 2) and needles (13) are straight, the latter having a length no shorter than the length of the intermediate cavities between adjacent teeth of each jaw (1, 2).

4. The instrument of claim 2, characterized in that each drum (5, 6) is provided, for the winding of flexible wires (16, 17), with a circumferential slot (21) closed by a fixed cover (22, 23), said covers being each provided with a short slot (24), said slots (24) communicating with thin channels (19, 20) managed through said support members (3, 4), said thin channels (19, 20) slidably receiving flexible wires (16, 17) while the latter unwind out of circumferential slots (21) when knob (7) is rotated in the unwinding direction.

5. The instrument of claim 4, characterized in that said fixed covers (22, 23) of the pair of drums (5, 6) are provided with a central opening (25), and through each of said openings there is received a hub (26) integral with each drum (5, 6) and in that said hubs (26) are provided with coupling means (27) adapted to engage or disengage said drums (5, 6) relative to each other, whereby said drums may be rotated as an integral assembly by means of said knob (7), in the direction of unwinding said wires (16, 17) out of said circumferential slots (21).

6. The instrument of claim 4, characterized in that said thin channels (19, 20) wherein flexible wires (16, 17) are slidably received, may be provided in the molding stage of said supports (3, 4) or they may be applied thereto as small gauge tubes.

7. The instrument of claim 3, characterized in that each jaw (1, 2) forms an angle relative to its own support member (3, 4) through a circularly radiused transition part (18) wherein said flexible wires (16, 17) are slidably received and extend on one side towards said drums (5, 6) while on the opposite side they are fastened to said needles (13) and to the ends of suture thread (14), the latter being contained in a protective small diameter tube (15).

8. The instrument of claim 1, characterized in that said support members (3, 4) are hingedly connected to each other at the end located opposite to said jaws (1, 2) and in that one of said support members is provided with a first constant width longitudinal slot (31), while the other support member is provided with a second slot overlapping the first slot, and having the same width of the latter at the end thereof located on the side of the jaws (1, 2), whereas proceeding towards the support members hinged connection, said slot (32) gradually widens whereby a control knob (33) slidably received within both slots (31, 32), when located at the position where both slots have the same width, causes the pair of jaws (1, 2) to close, whereas at the position of larger width of said slot, the pair of support members (3, 4) and therefore jaws (1, 2) can open in order to enable the part to be sutured to be introduced therebetween.

9. The instrument of claim 2, characterized in that there is provided a disposable plastic material central core containing said flexible wires (16, 17), said nedlees (13) and said suture thread (14), said core being inserted between said pair of hingedly connected support members (3, 4), preferably made of metal, provided with jaws (1, 2) and with control drums (5, 6), said support members (3, 4) being adapted to be durably used, each time with a new central core.

10. The instrument of claim 2, characterized in that the diameter of said suture thread (14) is smaller than the height of said slots (12) and the latter height is smaller than the diameter of flexible wires (16, 17), and in that said diameter is smaller than the diameter of openings (10, 11) receiving needles (13) therethrough.

11. The instrument of claim 4, characterized in that the diameter of circumferential slots (21) of drums (5, 6) is such that, to a three quarter of a turn rotation of knob (7) there corresponds such a forward motion of flexible wires (16, 17) to make needles (13) to project out of free end (29) of said jaws (1, 2).

12. The instrument of claim 4, characterized in that between said drums (5, 6) and stationary covers (22, 23) there is provided means (34) adapted to prevent rotation of drums (5, 6) in a direction opposite to the unwinding direction of flexible wires (16, 17) relative to circumferential slots (21).

* * * * *